(12) United States Patent
Huang et al.

(10) Patent No.: US 10,533,160 B2
(45) Date of Patent: Jan. 14, 2020

(54) RECOMBINANT PROTEIN, AND PREPARATION METHOD AND APPLICATION THEREOF

(71) Applicant: Industrial Technology Research Institute, Hsinchu (TW)

(72) Inventors: Yi-Chau Huang, Hsinchu County (TW); Huai-Lo Lee, Hsinchu County (TW); Yu-Yin Tsai, Hsinchu (TW); Chih-Lung Lin, Taichung (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 15/838,361

(22) Filed: Dec. 12, 2017

(65) Prior Publication Data

US 2018/0163184 A1    Jun. 14, 2018

Related U.S. Application Data

(60) Provisional application No. 62/433,733, filed on Dec. 13, 2016.

(51) Int. Cl.
| | | |
|---|---|---|
| *C12N 9/02* | (2006.01) | |
| *C12N 9/06* | (2006.01) | |
| *C12Q 1/26* | (2006.01) | |
| *G01N 33/72* | (2006.01) | |

(52) U.S. Cl.
CPC ............ *C12N 9/0032* (2013.01); *C12Q 1/26* (2013.01); *G01N 2333/4713* (2013.01)

(58) Field of Classification Search
CPC . C12N 9/06; C12N 11/00; C12N 9/02; C12Q 1/26; G01N 33/72
See application file for complete search history.

(56) References Cited

U.S. PATENT DOCUMENTS

| 8,003,359 B2 | 8/2011 | Hirokawa et al. |
|---|---|---|
| 8,993,255 B2 | 3/2015 | Hirao et al. |
| 9,062,286 B2 | 6/2015 | Ichiyanagi et al. |
| 2004/0115662 A1 | 6/2004 | Sakaue et al. |
| 2012/0003678 A1 | 1/2012 | Aisaka et al. |
| 2014/0228914 A1 | 8/2014 | van de Ven et al. |
| 2014/0356928 A1 | 12/2014 | Masakari et al. |
| 2015/0062892 A1 | 3/2015 | Krames et al. |
| 2016/0366746 A1 | 12/2016 | van de Ven et al. |

FOREIGN PATENT DOCUMENTS

| CN | 102171338 | 8/2011 |
|---|---|---|
| CN | 102575278 | 7/2012 |
| EP | 2020439 | 2/2009 |
| EP | 2287295 | 2/2011 |
| EP | 2354224 | 8/2011 |
| TW | 200528716 | 9/2005 |

OTHER PUBLICATIONS

Ohm et al., UniProt accession No. M2TRN2, May 2013.*
Kozo Hirokawa, et al., "Enhancement of thermostability of fungal deglycating enzymes by directed evolution," Applied Microbiology and Biotechnology, vol. 78, Feb. 1, 2008, pp. 775-781.
Stefano Ferri, et al., "Engineering Fructosyl Peptide Oxidase to Improve Activity Toward the Fructosyl Hexapeptide Standard for HbA1c Measurement," Molecular Biotechnology, vol. 54, Jan. 20, 2013, pp. 939-943.
Seungsu Kim, et al., "Motif-Based Search for a Novel Fructosyl Peptide Oxidase From Genome Databases," Biotechnology and Bioengineering, vol. 106, No. 3, Jun. 15, 2010, pp. 358-366.
Federica Rigoldi, et al., "Molecular dynamics simulations provide insights into substrate specificity of FAOX family members," Molecular BioSystems, vol. 12, No. 8, Jul. 19, 2016, pp. 1-34.
Nobuyuki Yoshida, et al., "Primary structures of fungal fructosyl amino acid oxidases and their application to the measurement of glycated proteins," European Journal of Biochemistry, vol. 242, Dec. 15, 1996, pp. 499-505.
Yasuyoshi Sakai, et al., "Purification and Properties of Fructosyl Lysine Oxidase from Fusarium oxysporum S-1F4," Bioscience, Biotechnology, and Biochemistry, vol. 59, No. 3, Mar. 1995, pp. 487-491.
Zhanglin Lin, et al., "Occurrence, characteristics, and applications of fructosyl amine oxidases (amadoriases)," Applied Microbiology and Biotechnology, vol. 86, No. 3, Mar. 27, 2010, pp. 1613-1619.
"Search Report of Europe Counterpart Application", dated Apr. 3, 2018, p. 1-p. 6, in which the listed references were cited.
Miho Kameya et al., "Advancing the Development of Glycated Protein Biosensing Technology : Next-Generation Sensing Molecules", Journal of Diabetes Science and Technology, Mar. 17, 2015, pp. 183-191.
Hirokawa K et al., "Molecular cloning and expression of novel fructosyl peptide oxidases and their application for the measurement of glycated protein", Biochemical and Biophysical Research Communicat, Elsevier, Amsterdam, NL, Nov. 7, 2003, pp. 104-111.
"Search Report of Europe Counterpart Application", dated Feb. 22, 2019, pp. 1-13.

* cited by examiner

*Primary Examiner* — Maryam Monshipouri
(74) *Attorney, Agent, or Firm* — JCIPRNET

(57) ABSTRACT

A recombinant protein and a preparation method and application thereof are provided. The recombinant protein includes a peptide, and the peptide includes an amino acid sequence after substitution of the sequence of SEQ ID NO: 1. The substitution includes at least one selected from the group consisting of the following substitutions: the amino acid at position 182 of SEQ ID NO: 1 is substituted with aspartic acid (Asp); the amino acid at position 268 of SEQ ID NO: 1 is substituted with aspartic acid (Asp); and the amino acid at position 384 of SEQ ID NO: 1 is substituted with tyrosine (Tyr). The recombinant protein is suitable for detecting glycated hemoglobin.

10 Claims, 1 Drawing Sheet
Specification includes a Sequence Listing.

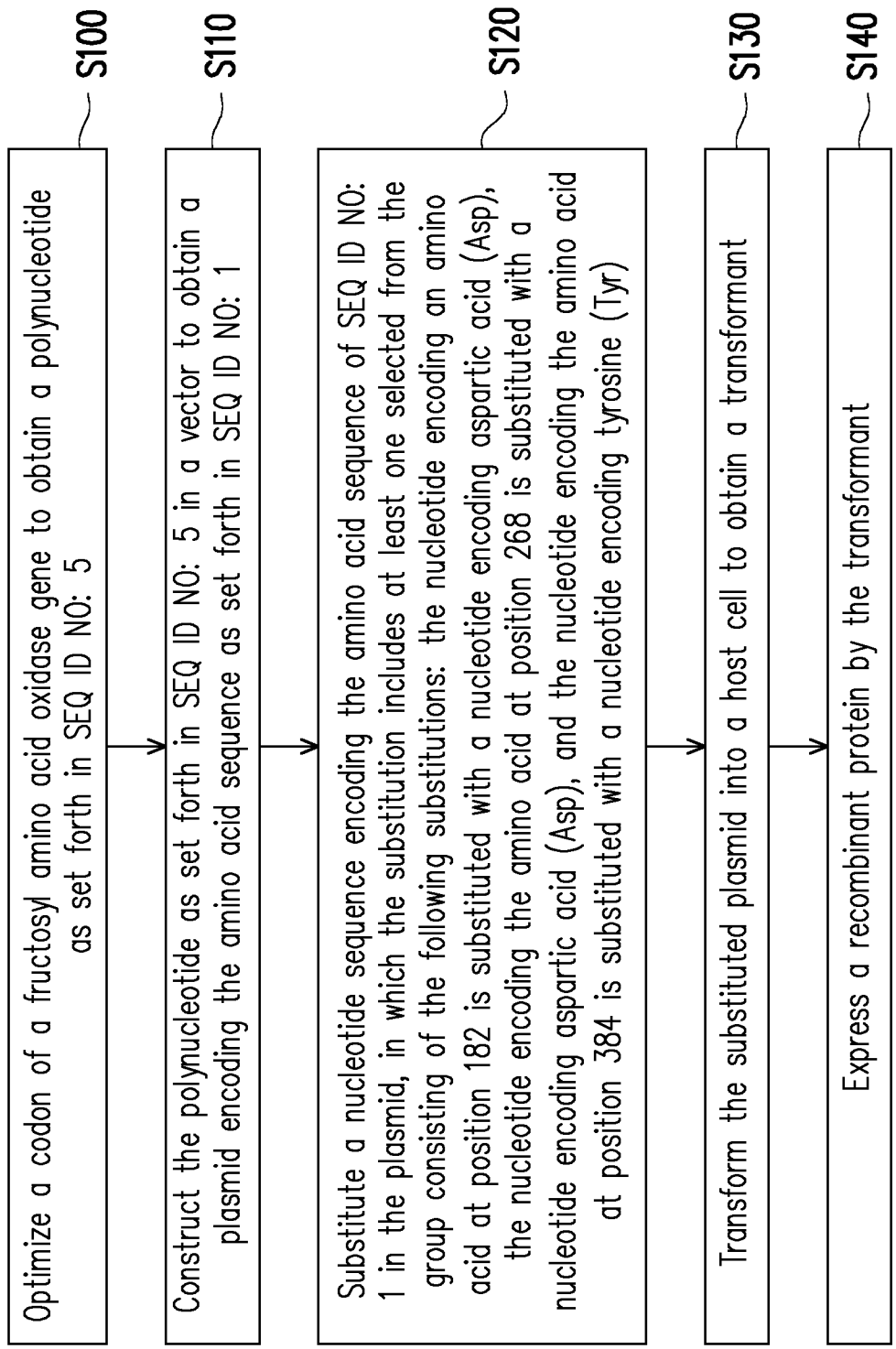

SEQUENCE LISTING

<160> NUMBER OF SEQ ID NOS: 11

<210> SEQ ID NO 1
<211> LENGTH: 437
<212> TYPE: PRT
<213> ORGANISM: Phaeosphaeria nodorum

<400> SEQUENCE: 1

-continued

```
Met Ala Pro Ser Arg Ala Asn Thr Ser Val Ile Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Val Thr Val Leu Asp Ala Tyr Pro Ile Pro Ser Ser
            35                  40                  45

Gln Ser Ala Gly Asn Asp Leu Asn Lys Ile Met Gly Val Ser Leu Arg
50                  55                  60

Asn Pro Val Asp Leu Gln Leu Ala Leu Glu Ala Arg Gln Met Trp Asn
65                  70                  75                  80

Glu Asp Glu Leu Phe Lys Lys Phe Phe His Asn Thr Gly Arg Leu Asp
                85                  90                  95

Cys Ala His Gly Glu Lys Asp Ile Ala Asp Leu Lys Ser Gly Tyr Gln
            100                 105                 110

Ala Leu Val Asp Ala Gly Leu Asp Ala Thr Asn Glu Trp Leu Asp Ser
            115                 120                 125

Glu Asp Glu Ile Leu Lys Arg Met Pro Leu Leu Ser Arg Asp Gln Ile
130                 135                 140

Lys Gly Trp Lys Ala Ile Phe Ser Lys Asp Gly Gly Trp Leu Ala Ala
145                 150                 155                 160

Ala Lys Ala Ile Asn Ala Val Gly Glu Tyr Leu Arg Asp Gln Gly Val
            165                 170                 175

Arg Phe Gly Phe Tyr Gly Ala Gly Ser Phe Lys Ala Pro Leu Leu Ala
            180                 185                 190

Glu Gly Val Cys Ile Gly Val Glu Thr Val Asp Gly Thr Arg Tyr Tyr
            195                 200                 205

Ala Asp Lys Val Val Leu Ala Ala Gly Ala Trp Ser Pro Thr Leu Val
210                 215                 220

Glu Leu His Glu Gln Cys Val Ser Lys Ala Trp Val Tyr Gly His Ile
225                 230                 235                 240

Gln Leu Thr Pro Glu Glu Ala Ala Arg Tyr Lys Asn Ser Pro Val Val
            245                 250                 255

Tyr Asn Gly Asp Val Gly Phe Phe Glu Pro Asn Glu His Gly Val
            260                 265                 270

Ile Lys Val Cys Asp Glu Phe Pro Gly Phe Thr Arg Phe Lys Met His
            275                 280                 285

Gln Pro Phe Gly Ala Lys Ala Pro Lys Arg Ile Ser Val Pro Arg Ser
            290                 295                 300

His Ala Lys His Pro Thr Asp Thr Ile Pro Asp Ala Ser Asp Val Ser
305                 310                 315                 320

Ile Arg Arg Ala Ile Ala Thr Phe Met Pro Gln Phe Lys Asn Lys Lys
            325                 330                 335

Met Phe Asn Gln Ala Met Cys Trp Cys Thr Asp Thr Ala Asp Ala Ala
            340                 345                 350

Leu Leu Ile Cys Glu His Pro Glu Trp Lys Asn Phe Val Leu Ala Thr
            355                 360                 365

Gly Asp Ser Gly His Ser Phe Lys Leu Leu Pro Asn Ile Gly Lys His
            370                 375                 380

Val Val Glu Leu Leu Glu Gly Thr Leu Ala Asp Leu Ala His Ala
385                 390                 395                 400

Trp Arg Trp Arg Pro Gly Ser Gly Asp Ala Leu Lys Ser Arg Arg Ser
                405                 410                 415

Ala Pro Ala Lys Asp Leu Ala Asp Met Pro Gly Trp Asn His Asp Lys
```

```
                    420                 425                 430
Pro Arg Ala Asn Leu
            435

<210> SEQ ID NO 2
<211> LENGTH: 437
<212> TYPE: PRT
<213> ORGANISM: Phaeosphaeria nodorum

<400> SEQUENCE: 2

Met Ala Pro Ser Arg Ala Asn Thr Ser Val Ile Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Val Thr Val Leu Asp Ala Tyr Pro Ile Pro Ser Ser
        35                  40                  45

Gln Ser Ala Gly Asn Asp Leu Asn Lys Ile Met Gly Val Ser Leu Arg
50                  55                  60

Asn Pro Val Asp Leu Gln Leu Ala Leu Glu Ala Arg Gln Met Trp Asn
65                  70                  75                  80

Glu Asp Glu Leu Phe Lys Lys Phe Phe His Asn Thr Gly Arg Leu Asp
                85                  90                  95

Cys Ala His Gly Glu Lys Asp Ile Ala Asp Leu Lys Ser Gly Tyr Gln
            100                 105                 110

Ala Leu Val Asp Ala Gly Leu Asp Ala Thr Asn Glu Trp Leu Asp Ser
        115                 120                 125

Glu Asp Glu Ile Leu Lys Arg Met Pro Leu Leu Ser Arg Asp Gln Ile
130                 135                 140

Lys Gly Trp Lys Ala Ile Phe Ser Lys Asp Gly Gly Trp Leu Ala Ala
145                 150                 155                 160

Ala Lys Ala Ile Asn Ala Val Gly Glu Tyr Leu Arg Asp Gln Gly Val
                165                 170                 175

Arg Phe Gly Phe Tyr Asp Ala Gly Ser Phe Lys Ala Pro Leu Leu Ala
            180                 185                 190

Glu Gly Val Cys Ile Gly Val Glu Thr Val Asp Gly Thr Arg Tyr Tyr
        195                 200                 205

Ala Asp Lys Val Val Leu Ala Ala Gly Ala Trp Ser Pro Thr Leu Val
210                 215                 220

Glu Leu His Glu Gln Cys Val Ser Lys Ala Trp Val Tyr Gly His Ile
225                 230                 235                 240

Gln Leu Thr Pro Glu Glu Ala Ala Arg Tyr Lys Asn Ser Pro Val Val
                245                 250                 255

Tyr Asn Gly Asp Val Gly Phe Phe Glu Pro Asn Glu His Gly Val
            260                 265                 270

Ile Lys Val Cys Asp Glu Phe Pro Gly Phe Thr Arg Phe Lys Met His
        275                 280                 285

Gln Pro Phe Gly Ala Lys Ala Pro Lys Arg Ile Ser Val Pro Arg Ser
290                 295                 300

His Ala Lys His Pro Thr Asp Thr Ile Pro Asp Ala Ser Asp Val Ser
305                 310                 315                 320

Ile Arg Arg Ala Ile Ala Thr Phe Met Pro Gln Phe Lys Asn Lys Lys
                325                 330                 335

Met Phe Asn Gln Ala Met Cys Trp Cys Thr Asp Thr Ala Asp Ala Ala
            340                 345                 350
```

```
Leu Leu Ile Cys Glu His Pro Glu Trp Lys Asn Phe Val Leu Ala Thr
            355                 360                 365

Gly Asp Ser Gly His Ser Phe Lys Leu Leu Pro Asn Ile Gly Lys His
    370                 375                 380

Val Val Glu Leu Leu Glu Gly Thr Leu Ala Asp Asp Leu Ala His Ala
385                 390                 395                 400

Trp Arg Trp Arg Pro Gly Ser Gly Asp Ala Leu Lys Ser Arg Arg Ser
                405                 410                 415

Ala Pro Ala Lys Asp Leu Ala Asp Met Pro Gly Trp Asn His Asp Lys
                420                 425                 430

Pro Arg Ala Asn Leu
        435

<210> SEQ ID NO 3
<211> LENGTH: 437
<212> TYPE: PRT
<213> ORGANISM: Phaeosphaeria nodorum

<400> SEQUENCE: 3

Met Ala Pro Ser Arg Ala Asn Thr Ser Val Ile Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Val Thr Val Leu Asp Ala Tyr Pro Ile Pro Ser Ser
        35                  40                  45

Gln Ser Ala Gly Asn Asp Leu Asn Lys Ile Met Gly Val Ser Leu Arg
    50                  55                  60

Asn Pro Val Asp Leu Gln Leu Ala Leu Glu Ala Arg Gln Met Trp Asn
65                  70                  75                  80

Glu Asp Glu Leu Phe Lys Lys Phe Phe His Asn Thr Gly Arg Leu Asp
                85                  90                  95

Cys Ala His Gly Glu Lys Asp Ile Ala Asp Leu Lys Ser Gly Tyr Gln
            100                 105                 110

Ala Leu Val Asp Ala Gly Leu Asp Ala Thr Asn Glu Trp Leu Asp Ser
        115                 120                 125

Glu Asp Glu Ile Leu Lys Arg Met Pro Leu Leu Ser Arg Asp Gln Ile
    130                 135                 140

Lys Gly Trp Lys Ala Ile Phe Ser Lys Asp Gly Gly Trp Leu Ala Ala
145                 150                 155                 160

Ala Lys Ala Ile Asn Ala Val Gly Glu Tyr Leu Arg Asp Gln Gly Val
                165                 170                 175

Arg Phe Gly Phe Tyr Asp Ala Gly Ser Phe Lys Ala Pro Leu Leu Ala
            180                 185                 190

Glu Gly Val Cys Ile Gly Val Glu Thr Val Asp Gly Thr Arg Tyr Tyr
        195                 200                 205

Ala Asp Lys Val Val Leu Ala Ala Gly Ala Trp Ser Pro Thr Leu Val
    210                 215                 220

Glu Leu His Glu Gln Cys Val Ser Lys Ala Trp Val Tyr Gly His Ile
225                 230                 235                 240

Gln Leu Thr Pro Glu Glu Ala Arg Tyr Lys Asn Ser Pro Val Val
                245                 250                 255

Tyr Asn Gly Asp Val Gly Phe Phe Glu Pro Asp Glu His Gly Val
            260                 265                 270

Ile Lys Val Cys Asp Glu Phe Pro Gly Phe Thr Arg Phe Lys Met His
        275                 280                 285
```

```
Gln Pro Phe Gly Ala Lys Ala Pro Lys Arg Ile Ser Val Pro Arg Ser
    290                 295                 300
His Ala Lys His Pro Thr Asp Thr Ile Pro Asp Ala Ser Asp Val Ser
305                 310                 315                 320
Ile Arg Arg Ala Ile Ala Thr Phe Met Pro Gln Phe Lys Asn Lys Lys
                325                 330                 335
Met Phe Asn Gln Ala Met Cys Trp Cys Thr Asp Thr Ala Asp Ala Ala
            340                 345                 350
Leu Leu Ile Cys Glu His Pro Glu Trp Lys Asn Phe Val Leu Ala Thr
        355                 360                 365
Gly Asp Ser Gly His Ser Phe Lys Leu Leu Pro Asn Ile Gly Lys His
    370                 375                 380
Val Val Glu Leu Leu Glu Gly Thr Leu Ala Asp Asp Leu Ala His Ala
385                 390                 395                 400
Trp Arg Trp Arg Pro Gly Ser Gly Asp Ala Leu Lys Ser Arg Arg Ser
                405                 410                 415
Ala Pro Ala Lys Asp Leu Ala Asp Met Pro Gly Trp Asn His Asp Lys
                420                 425                 430
Pro Arg Ala Asn Leu
        435

<210> SEQ ID NO 4
<211> LENGTH: 437
<212> TYPE: PRT
<213> ORGANISM: Phaeosphaeria nodorum

<400> SEQUENCE: 4

Met Ala Pro Ser Arg Ala Asn Thr Ser Val Ile Val Val Gly Gly Gly
1               5                   10                  15
Gly Thr Ile Gly Ser Ser Thr Ala Leu His Leu Val Arg Ser Gly Tyr
                20                  25                  30
Thr Pro Ser Asn Val Thr Val Leu Asp Ala Tyr Pro Ile Pro Ser Ser
            35                  40                  45
Gln Ser Ala Gly Asn Asp Leu Asn Lys Ile Met Gly Val Ser Leu Arg
    50                  55                  60
Asn Pro Val Asp Leu Gln Leu Ala Leu Glu Ala Arg Gln Met Trp Asn
65                  70                  75                  80
Glu Asp Glu Leu Phe Lys Lys Phe Phe His Asn Thr Gly Arg Leu Asp
                85                  90                  95
Cys Ala His Gly Glu Lys Asp Ile Ala Asp Leu Lys Ser Gly Tyr Gln
            100                 105                 110
Ala Leu Val Asp Ala Gly Leu Asp Ala Thr Asn Glu Trp Leu Asp Ser
        115                 120                 125
Glu Asp Glu Ile Leu Lys Arg Met Pro Leu Leu Ser Arg Asp Gln Ile
    130                 135                 140
Lys Gly Trp Lys Ala Ile Phe Ser Lys Asp Gly Gly Trp Leu Ala Ala
145                 150                 155                 160
Ala Lys Ala Ile Asn Ala Val Gly Glu Tyr Leu Arg Asp Gln Gly Val
                165                 170                 175
Arg Phe Gly Phe Tyr Asp Ala Gly Ser Phe Lys Ala Pro Leu Leu Ala
            180                 185                 190
Glu Gly Val Cys Ile Gly Val Glu Thr Val Asp Gly Thr Arg Tyr Tyr
        195                 200                 205
Ala Asp Lys Val Val Leu Ala Ala Gly Ala Trp Ser Pro Thr Leu Val
```

```
                        210                 215                 220

Glu Leu His Glu Gln Cys Val Ser Lys Ala Trp Val Tyr Gly His Ile
225                 230                 235                 240

Gln Leu Thr Pro Glu Glu Ala Ala Arg Tyr Lys Asn Ser Pro Val Val
                    245                 250                 255

Tyr Asn Gly Asp Val Gly Phe Phe Glu Pro Asp Glu His Gly Val
                260                 265                 270

Ile Lys Val Cys Asp Glu Phe Pro Gly Phe Thr Arg Phe Lys Met His
            275                 280                 285

Gln Pro Phe Gly Ala Lys Ala Pro Lys Arg Ile Ser Val Pro Arg Ser
        290                 295                 300

His Ala Lys His Pro Thr Asp Thr Ile Pro Asp Ala Ser Asp Val Ser
305                 310                 315                 320

Ile Arg Arg Ala Ile Ala Thr Phe Met Pro Gln Phe Lys Asn Lys Lys
                    325                 330                 335

Met Phe Asn Gln Ala Met Cys Trp Cys Thr Asp Thr Ala Asp Ala Ala
                340                 345                 350

Leu Leu Ile Cys Glu His Pro Glu Trp Lys Asn Phe Val Leu Ala Thr
            355                 360                 365

Gly Asp Ser Gly His Ser Phe Lys Leu Leu Pro Asn Ile Gly Lys Tyr
        370                 375                 380

Val Val Glu Leu Leu Glu Gly Thr Leu Ala Asp Asp Leu Ala His Ala
385                 390                 395                 400

Trp Arg Trp Arg Pro Gly Ser Gly Asp Ala Leu Lys Ser Arg Arg Ser
                    405                 410                 415

Ala Pro Ala Lys Asp Leu Ala Asp Met Pro Gly Trp Asn His Asp Lys
                420                 425                 430

Pro Arg Ala Asn Leu
            435

<210> SEQ ID NO 5
<211> LENGTH: 1314
<212> TYPE: DNA
<213> ORGANISM: Artificial sequence
<220> FEATURE:
<223> OTHER INFORMATION: A polynucleotide encoding the amino acid
      sequence shown in SEQ ID NO: 1
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
```

-continued

```
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
```

```
<222> LOCATION: (99)..(99)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
```

```
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (219)..(219)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
```

-continued

```
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (456)..(456)
```

```
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t
<220> FEATURE:
<221> NAME/KEY: misc_feature
<222> LOCATION: (468)..(468)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
```

```
<222> LOCATION: (555)..(555)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (615)..(615)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
```

-continued

```
<221> NAME/KEY: misc_feature
<222> LOCATION: (648)..(648)
<223> OTHER INFORMATION: n is a, c, g, or t
<220> FEATURE:
<221> NAME/KEY: misc_feature
<222> LOCATION: (651)..(651)
<223> OTHER INFORMATION: n is a, c, g, or t
<220> FEATURE:
<221> NAME/KEY: misc_feature
<222> LOCATION: (654)..(654)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (672)..(672)
<223> OTHER INFORMATION: n is a, c, g, or t
<220> FEATURE:
<221> NAME/KEY: misc_feature
<222> LOCATION: (678)..(678)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (726)..(726)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (741)..(741)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t
```

-continued

```
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (786)..(786)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t
<220> FEATURE:
<221> NAME/KEY: misc_feature
<222> LOCATION: (813)..(813)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (825)..(825)
<223> OTHER INFORMATION: n is a, c, g, or t
<220> FEATURE:
<221> NAME/KEY: misc_feature
<222> LOCATION: (840)..(840)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (849)..(849)
<223> OTHER INFORMATION: n is a, c, g, or t
<220> FEATURE:
<221> NAME/KEY: misc_feature
<222> LOCATION: (852)..(852)
<223> OTHER INFORMATION: n is a, c, g, or t
<220> FEATURE:
<221> NAME/KEY: misc_feature
<222> LOCATION: (870)..(870)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (879)..(879)
<223> OTHER INFORMATION: n is a, c, g, or t
<220> FEATURE:
<221> NAME/KEY: misc_feature
<222> LOCATION: (885)..(885)
<223> OTHER INFORMATION: n is a, c, g, or t
<220> FEATURE:
<221> NAME/KEY: misc_feature
<222> LOCATION: (888)..(888)
```

```
<223> OTHER INFORMATION: n is a, c, g, or t
<220> FEATURE:
<221> NAME/KEY: misc_feature
<222> LOCATION: (894)..(894)
<223> OTHER INFORMATION: n is a, c, g, or t
<220> FEATURE:
<221> NAME/KEY: misc_feature
<222> LOCATION: (900)..(900)
<223> OTHER INFORMATION: n is a, c, g, or t
<220> FEATURE:
<221> NAME/KEY: misc_feature
<222> LOCATION: (903)..(903)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (909)..(909)
<223> OTHER INFORMATION: n is a, c, g, or t
<220> FEATURE:
<221> NAME/KEY: misc_feature
<222> LOCATION: (912)..(912)
<223> OTHER INFORMATION: n is a, c, g, or t
<220> FEATURE:
<221> NAME/KEY: misc_feature
<222> LOCATION: (918)..(918)
<223> OTHER INFORMATION: n is a, c, g, or t
<220> FEATURE:
<221> NAME/KEY: misc_feature
<222> LOCATION: (927)..(927)
<223> OTHER INFORMATION: n is a, c, g, or t
<220> FEATURE:
<221> NAME/KEY: misc_feature
<222> LOCATION: (930)..(930)
<223> OTHER INFORMATION: n is a, c, g, or t
<220> FEATURE:
<221> NAME/KEY: misc_feature
<222> LOCATION: (936)..(936)
<223> OTHER INFORMATION: n is a, c, g, or t
<220> FEATURE:
<221> NAME/KEY: misc_feature
<222> LOCATION: (942)..(942)
<223> OTHER INFORMATION: n is a, c, g, or t
<220> FEATURE:
<221> NAME/KEY: misc_feature
<222> LOCATION: (948)..(948)
<223> OTHER INFORMATION: n is a, c, g, or t
<220> FEATURE:
<221> NAME/KEY: misc_feature
<222> LOCATION: (951)..(951)
<223> OTHER INFORMATION: n is a, c, g, or t
<220> FEATURE:
<221> NAME/KEY: misc_feature
<222> LOCATION: (957)..(957)
<223> OTHER INFORMATION: n is a, c, g, or t
<220> FEATURE:
<221> NAME/KEY: misc_feature
<222> LOCATION: (960)..(960)
<223> OTHER INFORMATION: n is a, c, g, or t
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (969)..(969)
<223> OTHER INFORMATION: n is a, c, g, or t
<220> FEATURE:
<221> NAME/KEY: misc_feature
<222> LOCATION: (972)..(972)
<223> OTHER INFORMATION: n is a, c, g, or t
<220> FEATURE:
<221> NAME/KEY: misc_feature
<222> LOCATION: (978)..(978)
<223> OTHER INFORMATION: n is a, c, g, or t
<220> FEATURE:
<221> NAME/KEY: misc_feature
```

```
<222> LOCATION: (981)..(981)
<223> OTHER INFORMATION: n is a, c, g, or t
<220> FEATURE:
<221> NAME/KEY: misc_feature
<222> LOCATION: (990)..(990)
<223> OTHER INFORMATION: n is a, c, g, or t
<220> FEATURE:
<221> NAME/KEY: misc_feature
<222> LOCATION: (1023)..(1023)
<223> OTHER INFORMATION: n is a, c, g, or t
<220> FEATURE:
<221> NAME/KEY: misc_feature
<222> LOCATION: (1038)..(1038)
<223> OTHER INFORMATION: n is a, c, g, or t
<220> FEATURE:
<221> NAME/KEY: misc_feature
<222> LOCATION: (1044)..(1044)
<223> OTHER INFORMATION: n is a, c, g, or t
<220> FEATURE:
<221> NAME/KEY: misc_feature
<222> LOCATION: (1047)..(1047)
<223> OTHER INFORMATION: n is a, c, g, or t
<220> FEATURE:
<221> NAME/KEY: misc_feature
<222> LOCATION: (1053)..(1053)
<223> OTHER INFORMATION: n is a, c, g, or t
<220> FEATURE:
<221> NAME/KEY: misc_feature
<222> LOCATION: (1056)..(1056)
<223> OTHER INFORMATION: n is a, c, g, or t
<220> FEATURE:
<221> NAME/KEY: misc_feature
<222> LOCATION: (1059)..(1059)
<223> OTHER INFORMATION: n is a, c, g, or t
<220> FEATURE:
<221> NAME/KEY: misc_feature
<222> LOCATION: (1062)..(1062)
<223> OTHER INFORMATION: n is a, c, g, or t
<220> FEATURE:
<221> NAME/KEY: misc_feature
<222> LOCATION: (1077)..(1077)
<223> OTHER INFORMATION: n is a, c, g, or t
<220> FEATURE:
<221> NAME/KEY: misc_feature
<222> LOCATION: (1095)..(1095)
<223> OTHER INFORMATION: n is a, c, g, or t
<220> FEATURE:
<221> NAME/KEY: misc_feature
<222> LOCATION: (1098)..(1098)
<223> OTHER INFORMATION: n is a, c, g, or t
<220> FEATURE:
<221> NAME/KEY: misc_feature
<222> LOCATION: (1101)..(1101)
<223> OTHER INFORMATION: n is a, c, g, or t
<220> FEATURE:
<221> NAME/KEY: misc_feature
<222> LOCATION: (1104)..(1104)
<223> OTHER INFORMATION: n is a, c, g, or t
<220> FEATURE:
<221> NAME/KEY: misc_feature
<222> LOCATION: (1107)..(1107)
<223> OTHER INFORMATION: n is a, c, g, or t
<220> FEATURE:
<221> NAME/KEY: misc_feature
<222> LOCATION: (1113)..(1113)
<223> OTHER INFORMATION: n is a, c, g, or t
<220> FEATURE:
<221> NAME/KEY: misc_feature
<222> LOCATION: (1116)..(1116)
<223> OTHER INFORMATION: n is a, c, g, or t
<220> FEATURE:
<221> NAME/KEY: misc_feature
<222> LOCATION: (1122)..(1122)
<223> OTHER INFORMATION: n is a, c, g, or t
<220> FEATURE:
<221> NAME/KEY: misc_feature
<222> LOCATION: (1131)..(1131)
<223> OTHER INFORMATION: n is a, c, g, or t
<220> FEATURE:
```

```
<221> NAME/KEY: misc_feature
<222> LOCATION: (1134)..(1134)
<223> OTHER INFORMATION: n is a, c, g, or t
<220> FEATURE:
<221> NAME/KEY: misc_feature
<222> LOCATION: (1137)..(1137)
<223> OTHER INFORMATION: n is a, c, g, or t
<220> FEATURE:
<221> NAME/KEY: misc_feature
<222> LOCATION: (1146)..(1146)
<223> OTHER INFORMATION: n is a, c, g, or t
<220> FEATURE:
<221> NAME/KEY: misc_feature
<222> LOCATION: (1155)..(1155)
<223> OTHER INFORMATION: n is a, c, g, or t
<220> FEATURE:
<221> NAME/KEY: misc_feature
<222> LOCATION: (1158)..(1158)
<223> OTHER INFORMATION: n is a, c, g, or t
<220> FEATURE:
<221> NAME/KEY: misc_feature
<222> LOCATION: (1164)..(1164)
<223> OTHER INFORMATION: n is a, c, g, or t
<220> FEATURE:
<221> NAME/KEY: misc_feature
<222> LOCATION: (1167)..(1167)
<223> OTHER INFORMATION: n is a, c, g, or t
<220> FEATURE:
<221> NAME/KEY: misc_feature
<222> LOCATION: (1173)..(1173)
<223> OTHER INFORMATION: n is a, c, g, or t
<220> FEATURE:
<221> NAME/KEY: misc_feature
<222> LOCATION: (1176)..(1176)
<223> OTHER INFORMATION: n is a, c, g, or t
<220> FEATURE:
<221> NAME/KEY: misc_feature
<222> LOCATION: (1179)..(1179)
<223> OTHER INFORMATION: n is a, c, g, or t
<220> FEATURE:
<221> NAME/KEY: misc_feature
<222> LOCATION: (1182)..(1182)
<223> OTHER INFORMATION: n is a, c, g, or t
<220> FEATURE:
<221> NAME/KEY: misc_feature
<222> LOCATION: (1191)..(1191)
<223> OTHER INFORMATION: n is a, c, g, or t
<220> FEATURE:
<221> NAME/KEY: misc_feature
<222> LOCATION: (1194)..(1194)
<223> OTHER INFORMATION: n is a, c, g, or t
<220> FEATURE:
<221> NAME/KEY: misc_feature
<222> LOCATION: (1200)..(1200)
<223> OTHER INFORMATION: n is a, c, g, or t
<220> FEATURE:
<221> NAME/KEY: misc_feature
<222> LOCATION: (1206)..(1206)
<223> OTHER INFORMATION: n is a, c, g, or t
<220> FEATURE:
<221> NAME/KEY: misc_feature
<222> LOCATION: (1212)..(1212)
<223> OTHER INFORMATION: n is a, c, g, or t
<220> FEATURE:
<221> NAME/KEY: misc_feature
<222> LOCATION: (1215)..(1215)
<223> OTHER INFORMATION: n is a, c, g, or t
<220> FEATURE:
<221> NAME/KEY: misc_feature
<222> LOCATION: (1218)..(1218)
<223> OTHER INFORMATION: n is a, c, g, or t
<220> FEATURE:
<221> NAME/KEY: misc_feature
<222> LOCATION: (1221)..(1221)
<223> OTHER INFORMATION: n is a, c, g, or t
<220> FEATURE:
<221> NAME/KEY: misc_feature
<222> LOCATION: (1224)..(1224)
<223> OTHER INFORMATION: n is a, c, g, or t
```

-continued

<220> FEATURE:
<221> NAME/KEY: misc_feature
<222> LOCATION: (1230)..(1230)
<223> OTHER INFORMATION: n is a, c, g, or t
<220> FEATURE:
<221> NAME/KEY: misc_feature
<222> LOCATION: (1233)..(1233)
<223> OTHER INFORMATION: n is a, c, g, or t
<220> FEATURE:
<221> NAME/KEY: misc_feature
<222> LOCATION: (1239)..(1239)
<223> OTHER INFORMATION: n is a, c, g, or t
<220> FEATURE:
<221> NAME/KEY: misc_feature
<222> LOCATION: (1242)..(1242)
<223> OTHER INFORMATION: n is a, c, g, or t
<220> FEATURE:
<221> NAME/KEY: misc_feature
<222> LOCATION: (1245)..(1245)
<223> OTHER INFORMATION: n is a, c, g, or t
<220> FEATURE:
<221> NAME/KEY: misc_feature
<222> LOCATION: (1248)..(1248)
<223> OTHER INFORMATION: n is a, c, g, or t
<220> FEATURE:
<221> NAME/KEY: misc_feature
<222> LOCATION: (1251)..(1251)
<223> OTHER INFORMATION: n is a, c, g, or t
<220> FEATURE:
<221> NAME/KEY: misc_feature
<222> LOCATION: (1254)..(1254)
<223> OTHER INFORMATION: n is a, c, g, or t
<220> FEATURE:
<221> NAME/KEY: misc_feature
<222> LOCATION: (1257)..(1257)
<223> OTHER INFORMATION: n is a, c, g, or t
<220> FEATURE:
<221> NAME/KEY: misc_feature
<222> LOCATION: (1266)..(1266)
<223> OTHER INFORMATION: n is a, c, g, or t
<220> FEATURE:
<221> NAME/KEY: misc_feature
<222> LOCATION: (1269)..(1269)
<223> OTHER INFORMATION: n is a, c, g, or t
<220> FEATURE:
<221> NAME/KEY: misc_feature
<222> LOCATION: (1278)..(1278)
<223> OTHER INFORMATION: n is a, c, g, or t
<220> FEATURE:
<221> NAME/KEY: misc_feature
<222> LOCATION: (1281)..(1281)
<223> OTHER INFORMATION: n is a, c, g, or t
<220> FEATURE:
<221> NAME/KEY: misc_feature
<222> LOCATION: (1299)..(1299)
<223> OTHER INFORMATION: n is a, c, g, or t
<220> FEATURE:
<221> NAME/KEY: misc_feature
<222> LOCATION: (1302)..(1302)
<223> OTHER INFORMATION: n is a, c, g, or t
<220> FEATURE:
<221> NAME/KEY: misc_feature
<222> LOCATION: (1305)..(1305)
<223> OTHER INFORMATION: n is a, c, g, or t
<220> FEATURE:
<221> NAME/KEY: misc_feature
<222> LOCATION: (1311)..(1311)
<223> OTHER INFORMATION: n is a, c, g, or t

<400> SEQUENCE: 5
atggcnccnw snmgngcnaa yacnwsngtn athgtngtng gnggnggngg nacnathggn 60
wsnwsnacng cnytncayyt ngtnmgnwsn ggntayacnc cnwsnaaygt nacngtnytn 120
gaygcntayc cnathccnws nwsncarwsn gcnggnaayg ayytnaayaa rathatgggn 180
gtnwsnytnm gnaayccngt ngayytncar ytngcnytng argcnmgnca ratgtggaay 240

```
gargaygary tnttyaaraa rttyttycay aayacnggnm gnytngaytg ygcncayggn      300
garaargaya thgcngayyt naarwsnggn taycargcny tngtngaygc nggnytngay      360
gcnacnaayg artggytnga ywsngargay garathytna armgnatgcc nytnytnwsn      420
mgngaycara thaarggntg gaargcnath ttywsnaarg ayggnggntg gytngcngcn      480
gcnaargcna thaaygcngt nggngartay ytnmgngayc arggngtnmg nttyggntty      540
tayggngcng gnwsnttyaa rgcnccnytn ytngcngarg gngtntgyat hggngtngar      600
acngtngayg gnacnmgnta ytaygcngay aargtngtny tngcngcngg ngcntggwsn      660
ccnacnytng tngarytnca ygarcartgy gtnwsnaarg cntgggtnta yggncayath      720
carytnacnc cngargargc ngcnmgntay aaraaywsnc cngtngtnta yaayggngay      780
gtnggnttyt tyttygarcc naaygarcay ggngtnatha argtntgyga ygarttyccn      840
ggnttyacnm gnttyaarat gcaycarccn ttyggngcna argcnccnaa rmgnathwsn      900
gtnccnmgnw sncaygcnaa rcayccnacn gayacnathc cngaygcnws ngaygtnwsn      960
athmgnmgng cnathgcnac nttyatgccn carttyaara ayaaraarat gttyaaycar     1020
gcnatgtgyt ggtgyacnga yacngcngay gcngcnytny tnathtgyga rcayccngar     1080
tggaaraayt tygtnytngc nacnggngay wsnggncayw snttyaaryt nytnccnaay     1140
athggnaarc aygtngtnga rytnytngar ggnacnytng cngaygayyt ngcncaygcn     1200 tggmcgntggm gnccnggnws nggngaygcn ytnaarwsnm gnmgnwsngc nccngcnaar     1260
gayytngcng ayatgccngg ntggaaycay gayaarccnm gngcnaayyt ntag           1314

<210> SEQ ID NO 6
<211> LENGTH: 35
<212> TYPE: DNA
<213> ORGANISM: Artificial Sequence
<220> FEATURE:
<223> OTHER INFORMATION: Primer for the substitution of nucleotides
      encoding glycine at position 182 of SEQ ID NO: 1

<400> SEQUENCE: 6
gtgtacgttt cggtttctat gacgcgggct ctttc                                35

<210> SEQ ID NO 7
<211> LENGTH: 35
<212> TYPE: DNA
<213> ORGANISM: Artificial sequence
<220> FEATURE:
<223> OTHER INFORMATION: Primer for the substitution of nucleotides
      encoding glycine at position 182 of SEQ ID NO: 1

<400> SEQUENCE: 7
gaaagagccc gcgtcataga aaccgaaacg tacac                                35

<210> SEQ ID NO 8
<211> LENGTH: 29
<212> TYPE: DNA
<213> ORGANISM: Artificial sequence
<220> FEATURE:
<223> OTHER INFORMATION: Primer for the substitution of the nucleotide
      encoding asparagine at position 268 of SEQ ID NO: 1

<400> SEQUENCE: 8
ttttcttcga gccggacgag cacggcgtg                                       29

<210> SEQ ID NO 9
<211> LENGTH: 29
<212> TYPE: DNA
```

-continued

```
<213> ORGANISM: Artificial sequence
<220> FEATURE:
<223> OTHER INFORMATION: Primer for the substitution of the nucleotide
      encoding asparagine at position 268 of SEQ ID NO: 1

<400> SEQUENCE: 9
cacgccgtgc tcgtccggct cgaagaaaa                                   29

<210> SEQ ID NO 10
<211> LENGTH: 37
<212> TYPE: DNA
<213> ORGANISM: Artificial sequence
<220> FEATURE:
<223> OTHER INFORMATION: Primer for the substitution of the nucleotide
      encoding histidine at position 384 of SEQ ID NO: 1

<400> SEQUENCE: 10
ctgccaaata ttggcaagta tgttgttgaa ctgctgg                          37

<210> SEQ ID NO 11
<211> LENGTH: 37
<212> TYPE: DNA
<213> ORGANISM: Artificial sequence
<220> FEATURE:
<223> OTHER INFORMATION: Primer for the substitution of the nucleotide
      encoding histidine at position 384 of SEQ ID NO: 1

<400> SEQUENCE: 11
ccagcagttc aacaacatac ttgccaatat ttggcag                          37
```

RECOMBINANT PROTEIN, AND PREPARATION METHOD AND APPLICATION THEREOF

CROSS-REFERENCE TO RELATED APPLICATION

This application claims the priority benefits of U.S. provisional application Ser. No. 62/433,733, filed on Dec. 13, 2016. The entirety of the above-mentioned patent application is hereby incorporated by reference herein and made a part of this specification.

INCORPORATION BY REFERENCE OF SEQUENCE LISTING

A sequence listing submitted as a text file via EFS-Web is incorporated herein by reference. The text file containing the sequence listing is named "66204-US-sequence listing_ST25.txt"; its date of creation is Dec. 7, 2017; and its size is 37 kilobytes.

TECHNICAL FIELD

The disclosure relates to a recombinant protein and a preparation method and application thereof, and more particularly, to a recombinant protein suitable for detecting glycated hemoglobin.

BACKGROUND

For diabetics, the evaluation of the treatment or control effect of blood glucose includes using hemoglobin A1c (HbA1c) as the best detection target, and an enzyme method is used as the routine clinical detection method. The detection principle of the enzyme method is based on the glycolysis of fructosyl amino acid oxidase (FAOD), in which FAOD is used as the main reaction enzyme, and fructosyl valine (F-V) and fructosyl valyl histidine (F-VH) are used as the reaction substrates to perform the detection of glycated hemoglobin.

Therefore, during glycated hemoglobin detection using an enzyme method, substrate specificity of the fructosyl amino acid oxidase mainly acting as the main reaction enzyme is an essential factor. However, during the hydrolysis of glycated hemoglobin by protease, in addition to the production of F-V and F-VH, a large quantity of fructosyl lysine (F-K) is also relatively produced, and the current FAOD on the market still has a certain affinity for F-K, such that the detection of glycated hemoglobin is affected.

Moreover, the thermal stability of fructosyl amino acid oxidase in the detection kit for detecting glycated hemoglobin on the current market, is less than ideal, and a large amount of stabilizer is often added to the detection kit to improve the stability. However, diagnostic reagents require a certain period of time for storage, such that the requirement for stability is higher. In addition, the stabilizer added thereof often leads to an increase in reagent viscosity, thus affecting subsequent detection.

Therefore, a fructosyl amino acid oxidase with high substrate specificity and thermal stability is urgently needed to accurately quantify glycated hemoglobin and achieve long-term stable preservation.

SUMMARY

The disclosure provides a recombinant protein which may have higher thermal stability and substrate specificity.

The disclosure also provides a preparation method of a recombinant protein to prepare the above-mentioned recombinant protein.

The disclosure further provides a detection kit for detecting glycated hemoglobin having the advantages of accurately quantifying the glycated hemoglobin and long-term stable preservation.

The disclosure provides a recombinant protein including a peptide, in which the peptide includes an amino acid sequence after substitution of a sequence as set forth in SEQ ID NO: 1. The above-mentioned substitution may include at least one selected from the group consisting of the following substitutions: the amino acid at position 182 of SEQ ID NO: 1 is substituted with aspartic acid (Asp), the amino acid at position 268 of SEQ ID NO: 1 is substituted with aspartic acid (Asp), and the amino acid at position 384 of SEQ ID NO: 1 is substituted with tyrosine (Tyr).

In an embodiment of the disclosure, the substitution may include at least one selected from the group consisting of the following substitutions: the amino acid at position 182 of SEQ ID NO: 1 is substituted from glycine (Gly) to aspartic acid (Asp) (Gly182Asp), the amino acid at position 268 of SEQ ID NO: 1 is substituted from asparagine (Asn) to aspartic acid (Asp) (Asn268Asp), and the amino acid at position 384 of SEQ ID NO: 1 is substituted from histidine (His) to tyrosine (Tyr) (His384Tyr).

In an embodiment of the disclosure, the amino acid sequence of the peptide may include a sequence as set forth in SEQ ID NO: 2.

In an embodiment of the disclosure, the amino acid sequence of the peptide may include a sequence as set forth in SEQ ID NO: 3.

In an embodiment of the disclosure, the amino acid sequence of the peptide may include a sequence as set forth in SEQ ID NO: 4.

In an embodiment of the disclosure, the amino acid sequence of SEQ ID NO: 1 and a polynucleotide encoding the sequence of SEQ ID NO: 1 may be selected from *Phaeosphaeria nodorum*.

The disclosure further provides a preparation method of a recombinant protein, including the following steps: substituting a nucleotide sequence which may encode the amino acid sequence as set forth in SEQ ID NO: 1 in a plasmid. In which, the substitution includes at least one selected from the group consisting of the following substitutions: the nucleotide encoding the amino acid at position 182 is substituted with the nucleotide encoding aspartic acid (Asp), the nucleotide encoding the amino acid at position 268 is substituted with the amino acid encoding aspartic acid (Asp), and the nucleotide encoding the amino acid at position 384 is substituted with the nucleotide encoding tyrosine (Tyr). Next, the substituted plasmid is transformed into a host cell to obtain a transformant, and then the above-mentioned recombinant protein is expressed by the transformant.

In an embodiment of the disclosure, the substitution includes at least one selected from the group consisting of the following substitutions: the nucleotide encoding the amino acid at position 182 is substituted from the nucleotide encoding glycine (Gly) to the nucleotide encoding aspartic acid (Asp), the nucleotide encoding the amino acid at position 268 is substituted from the nucleotide encoding asparagine (Asn) to the nucleotide encoding aspartic acid (Asp), and the nucleotide encoding the amino acid at position 384 is substituted from the nucleotide encoding histidine (His) to the nucleotide encoding tyrosine (Tyr).

In an embodiment of the disclosure, the step of substituting the nucleotide encoding the amino acid includes: substituting the nucleotide encoding glycine (Gly) at position 182 via a primer as set forth in SEQ ID NO: 6 and a primer as set forth in SEQ ID NO: 7, substituting the nucleotide encoding asparagine (Asn) at position 268 via a primer as set forth in SEQ ID NO: 8 and a primer as set forth in a SEQ ID NO: 9, and substituting the nucleotide encoding histidine (His) at position 384 via a primer as set forth in SEQ ID NO: 10 and a primer as set forth in SEQ ID NO: 11.

In an embodiment of the disclosure, after the nucleotide encoding glycine (Gly) at position 182 is substituted, a recombinant protein containing the amino acid sequence as set forth in SEQ ID NO: 2 may be obtained.

In an embodiment of the disclosure, after the nucleotide encoding glycine (Gly) at position 182 and the nucleotide encoding asparagine (Asn) at position 268 are substituted simultaneously, a recombinant protein containing the amino acid sequence as set forth in SEQ ID NO: 3 may be obtained.

In an embodiment of the disclosure, after the nucleotide encoding glycine (Gly) at position 182, the nucleotide encoding asparagine (Asn) at position 268, and the nucleotide encoding histidine (His) at position 384 are substituted simultaneously, a recombinant protein containing the amino acid sequence as set forth in SEQ ID NO: 4 may be obtained.

In an embodiment of the disclosure, the method of preparing the above-mentioned plasmid may include: optimizing a codon of a fructosyl amino acid oxidase gene to obtain a polynucleotide as set forth in SEQ ID NO:5, and constructing the polynucleotide as set forth in SEQ ID NO:5 in a vector to obtain a plasmid encoding the amino acid sequence as set forth in SEQ ID NO: 1.

In an embodiment of the disclosure, the above-mentioned fructosyl amino acid oxidase gene may be selected from *Phaeosphaeria nodorum*.

The disclosure also provides a polynucleotide encoding the above-mentioned recombinant protein.

The disclosure further provides a recombinant vector, which includes the above-mentioned polynucleotide.

The disclosure further provides a transformant, which is obtained by transforming the above-mentioned recombinant vector into a host cell.

The disclosure further provides a detection kit for detecting glycated hemoglobin, in which the detection kit includes the above-mentioned recombinant protein.

Based on the above, the disclosure provides a recombinant protein and a preparation method thereof, in which the recombinant protein is obtained by substituting at least one amino acid of the amino acids at positions 182, 268, and 384 of the amino acid sequence as set forth in SEQ ID NO: 1. Moreover, in comparison to the wild-type fructosyl amino acid oxidase, this recombinant protein exhibits higher thermal stability and substrate specificity. Otherwise, in comparison to the commercial detection kit for detecting glycated hemoglobin, due to that the detection kit provided by the disclosure includes the above-mentioned recombinant protein, the advantages of accurately quantifying glycated hemoglobin and long-term stable preservation are provided accordingly.

Several exemplary embodiments accompanied with FIGURES are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

FIG. 1 illustrates the preparation process of a recombinant protein according to an embodiment of the disclosure.

DETAILED DESCRIPTION OF DISCLOSED EMBODIMENTS

FIG. 1 is a flowchart illustrating a preparation method of a recombinant protein according to an embodiment of the disclosure. First, referring to FIG. 1, as shown in step S100, codon optimization may be performed on a fructosyl amino acid oxidase gene to obtain the polynucleotide as set forth in SEQ ID NO: 5. The above-mentioned fructosyl amino acid oxidase gene may be selected from bacteria, yeast, or fungus, such as selected from *Phaeosphaeria nodorum*, but it is not limited thereto. For example, it may also be selected from *Aspergillus*, *Penicillium*, *Fusarium*, *Pichia*, *Coniochaeta*, *Eupencillum*, or *Corynebacterium*. In an embodiment, the above-mentioned fructosyl amino acid oxidase gene may be selected from *Phaeosphaeria nodorum*. In particular, the method of codon optimization includes adjusting the nucleotide in the codon, such as adjusting GGT to GGC such that the adjusted codon is suitable for being utilized in a new host cell and an amino acid may be expressed in large quantities. Moreover, this amino acid is the same as the amino acid expressed by the codon before adjustment.

The above-mentioned fructosyl amino acid oxidase may also be refer ed to as, for instance, fructosyl valine oxidase, fructosyl peptide oxidase (FPOX), amadoriase or ketoamine oxidase.

Next, as shown in step S110, the polynucleotide as set forth in SEQ ID NO: 5 may be constructed in a vector to obtain a plasmid encoding the amino acid sequence as set forth in SEQ ID NO: 1.

Thereafter, as shown in step S120, the nucleotide sequence encoding the amino acid sequence of SEQ ID NO: 1 in the plasmid may be substituted, in which the substitution may include at least one selected from the group consisting of the following substitutions: the nucleotide encoding the amino acid at position 182 is substituted with the nucleotide encoding aspartic acid (Asp), the nucleotide encoding the amino acid at position 268 is substituted with the amino acid encoding aspartic acid (Asp), and the nucleotide encoding the amino acid at position 384 is substituted with the nucleotide encoding tyrosine (Tyr).

In detail, the substitution may include at least one selected from the group consisting of the following substitutions: the nucleotide encoding the amino acid at position 182 is substituted from the nucleotide encoding glycine (Gly) to the nucleotide encoding aspartic acid (Asp), the nucleotide encoding the amino acid at position 268 is substituted from the nucleotide encoding asparagine (Asn) to the nucleotide encoding aspartic acid (Asp), and the nucleotide encoding the amino acid at position 384 is substituted from the nucleotide encoding histidine (His) to the nucleotide encoding tyrosine (Tyr).

More specifically, the step of substituting the amino acid may include: substituting the nucleotide encoding glycine (Gly) at position 182 via a primer as set forth in SEQ ID NO: 6 and a primer as set forth in SEQ ID NO: 7, substituting the nucleotide encoding asparagine (Asn) at position 268 via a primer as set forth in SEQ ID NO: 8 and a primer as set forth in SEQ ID NO: 9, and substituting the nucleotide encoding histidine (His) at position 384 via a primer as set forth in SEQ ID NO: 10 and a primer as set forth in SEQ ID NO: 11.

Next, as shown in step S130, transformation may be performed on the above-mentioned substituted plasmid into a host cell to obtain a transformant.

Thereafter, as shown in step S140, expression a recombinant protein by the above-mentioned transformant may be performed. The above-mentioned recombinant protein may include a peptide, and the peptide may include an amino acid sequence after substitution of the sequence as set forth in the SEQ ID NO: 1. The substitution may include at least one selected from the group consisting of the following substitutions: the amino acid at position 182 of SEQ ID NO: 1 is substituted with aspartic acid (Asp); the amino acid at position 268 of SEQ ID NO: 1 is substituted with aspartic acid (Asp); and the amino acid at position 384 of SEQ ID NO: 1 is substituted with tyrosine (Tyr).

In detail, the substitution may include at least one selected from the group consisting of the following substitutions: the amino acid at position 182 of SEQ ID NO: 1 is substituted from glycine (Gly) to aspartic acid (Asp) (Gly182Asp), the amino acid at position 268 of SEQ ID NO: 1 is substituted from asparagine (Asn) to aspartic acid (Asp) (Asn268Asp), and the amino acid at position 384 of SEQ ID NO: 1 is substituted from histidine (His) to tyrosine (Tyr) (His384Tyr).

In an embodiment, the preparation method as shown in steps S100 to S140 may be performed to obtain a recombinant protein. The recombinant protein is further described below.

In an embodiment, the recombinant protein includes a peptide, in which the peptide includes an amino acid sequence after substitution of a sequence as set forth in SEQ ID NO: 1. The above-mentioned substitution may include substituting at least one of glycine at position 182, asparagine (Asn) at position 268, and histidine (His) at position 384 of the amino acid sequence as set forth in SEQ ID NO: 1. In an embodiment, the substitution may include substituting the glycine at position 182 of SEQ ID NO: 1 with aspartic acid (Asp). In another embodiment, the substitution may include substituting the asparagine at position 268 of SEQ ID NO: 1 with aspartic acid (Asp). In yet another embodiment, the substitution may include substituting the histidine (His) at position 384 of SEQ ID NO: 1 with tyrosine (Tyr).

In an embodiment, the amino acid sequence as set forth in SEQ ID NO: 1 and the polynucleotide encoding the amino acid sequence as set forth in SEQ ID NO: 1 may be selected from *Phaeosphaeria nodorum*.

Specifically, in an embodiment, glycine at position 182 of the amino acid sequence as set forth in SEQ ID NO: 1 may be substituted to obtain the recombinant protein containing the amino acid sequence as set forth in SEQ ID NO: 2. In another embodiment, glycine at position 182 and asparagine (Asn) at position 268 of the amino acid sequence as set forth in SEQ ID NO: 1 may be substituted simultaneously to obtain the recombinant protein containing the amino acid sequence as set forth in SEQ ID NO: 3. In yet another embodiment, glycine at position 182, asparagine (Asn) at position 268, and histidine (His) at position 384 of the amino acid sequence as set forth in SEQ ID NO: 1 may be substituted simultaneously to obtain the recombinant protein containing the amino acid sequence as set forth in SEQ ID NO: 4.

In an embodiment, the above-mentioned recombinant protein may be fructosyl amino acid oxidase with oxidase activity for F-K, F-V, and F-VH, and is therefore suitable for detecting glycated hemoglobin. In another embodiment, in comparison to wild-type fructosyl amino acid oxidase, the recombinant protein containing the amino acid sequence as set forth in SEQ ID NO: 4 may have lower substrate specificity for F-K but higher substrate specificity for F-V and F-VH.

Moreover, in other embodiments, a polynucleotide, recombinant vector, transformant, and detection kit are further provided. The above-mentioned polynucleotide may be a polynucleotide encoding the above-mentioned recombinant protein, in which the polynucleotide may be a polynucleotide containing the nucleotide sequence as set forth in SEQ ID NO: 5. The above-mentioned recombinant vector may include the above-mentioned polynucleotide. The above-mentioned transformant may be obtained by transforming the above-mentioned recombinant vector into a host cell. The above-mentioned detection kit is suitable for detecting glycated hemoglobin and includes the above-mentioned recombinant protein.

EXPERIMENTS

Experiment 1: Synthesis of Fructosyl Amino Acid Oxidase Gene

First, a gene expected to encode fructosyl amino acid oxidase of *Phaeosphaeria nodorum* is selected from the genome database (ncbi.nlm.nih.gov/) of the National Center for Biotechnology Information (NCBI), such as a gene encoding a FAD-dependent oxidoreductase, and the results are similar to the mRNA shown in NCBI accession No. XM_001798659.1 (NCBI access number XM_001798659.1).

Next, for the cDNA corresponding to the above-mentioned mRNA, the cutting sites required for replication were designed at both ends thereof, and a codon thereof was optimized to a codon suitable to be expressed in a host cell. For instance, the codon was optimized to be suitable to be expressed in *E. coli*, and then the whole-genome synthesis was performed.

Next, the synthetic gene was sub-replicated in a vector, such as the EcoRV site of pUC57 (Genescript), and sequence analysis was perfoiiued on the cDNA portion replicated in the vector pUC57 to obtain the polynucleotide as set forth in SEQ ID NO: 5. In other words, the cDNA portion of the synthetic gene is the polynucleotide as set forth in SEQ ID NO: 5. The cDNA encoding region in the polynucleotide as set forth in SEQ ID NO: 5 was ranging from nucleotide NO. 1 to nucleotide NO. 1314, in which the start codon was corresponding to nucleotide NO. 1 to nucleotide NO. 3, and the stop codon TAG was corresponding to nucleotide NO. 1312 to nucleotide NO. 1314.

Experiment 2: Preparation of Plasmid Containing the Fructosyl Amino Acid Oxidase Gene The polynucleotide as set forth in SEQ ID NO: 5 was constructed into a vector by a cloning method, in which the vector is, for instance, pQE-30 (Qiagen), but the disclosure is not limited thereto.

Specifically, the polynucleotide as set forth in SEQ ID NO: 5 was replicated to the NcoI-SacI site of the vector pQE-30 via T4 DNA ligase by the NcoI restriction site introduced at the N-terminal during whole-genome synthesis and the SacI restriction site after the C-terminal stop codon to obtain the plasmid pYC1 expressing the amino acid sequence as set forth in SEQ ID NO: 1.

Experiment 3: Performing Site-Directed Mutagenesis on Fructosyl Amino Acid Oxidase The above-mentioned site-directed mutagenesis refers to substituting one of the amino acid residues of FAOD, such as substituting glycine (Gly) at position 182 of the amino acid sequence as set forth in SEQ ID NO: 1 to obtain a single-mutant fructosyl amino acid oxidase. Specifically, for instance, glycine at position 182 was substituted with aspartic acid (Asp). The method of substituting the amino acid residues includes, for instance, using a QuikChange Lightning Site-Directed Mutagenesis Kit (Agilent), but the disclosure is not limited thereto.

In particular, the polynucleotide encoding the amino acid sequence as set forth in SEQ ID NO: 1 is SEQ ID NO: 5. Accordingly, in an embodiment, firstly, the nucleotide encoding glycine (Gly) at position 182 of the amino acid sequence as set forth in SEQ ID NO: 1 was found to be ggc in the polynucleotide as set forth in SEQ ID NO: 5. At the same time, the primer as set forth in SEQ ID NO: 6 and the primer as set forth in SEQ ID NO: 7 were synthesized, in which both primers have the nucleotide gac. Next, a polymerase chain reaction (PCR) was performed on the plasmid pYC1 using the primer as set forth in SEQ ID NO: 6 and the primer as set forth in SEQ ID NO: 7 to obtain a recombinant plasmid. In the recombinant plasmid, the nucleotide ggc encoding glycine (Gly) at position 182 was substituted by the nucleotide gac encoding aspartic acid (Asp).

Thereafter, the recombinant plasmid was transformed by One Shot® Mach1™-T1R (Invitrogen) and 10 colonies exhibiting ampicillin resistance were selected, and then sequencing was performed on the nucleotide sequence of the 10 recombinant plasmids transformed into the 10 colonies to confirm whether the recombinant plasmids were successfully introduced to obtain a plasmid pHL35 expressing the amino acid sequence as set forth in SEQ ID NO: 2.

Experiment 4: Performing Multiple Point Mutations on Fructosyl Amino Acid Oxidase The above-mentioned multiple point mutation refers to substituting two of the amino acid residues of FAOD, such as substituting glycine (Gly) at position 182 and asparagine (Asn) at position 268 of the amino acid sequence as set forth in SEQ ID NO: 1 to obtain a double-mutant fructosyl amino acid oxidase. Specifically, for instance, glycine (Gly) at position 182 was substituted with aspartic acid (Asp) and asparagine (Asn) at position 268 was substituted with aspartic acid (Asp) at the same time. The method of substituting the amino acid residues is the same as above and is not repeated herein.

In particular, firstly, the nucleotide encoding asparagine (Asp) at position 268 of the amino acid sequence as set forth in SEQ ID NO: 1 was found to be aac in the polynucleotide as set forth in SEQ ID NO: 5. At the same time, the primer as set forth in SEQ ID NO: 8 and the primer as set forth in SEQ ID NO: 9 were synthesized, in which both primers have the nucleotide gac. Next, since the nucleotide encoding the amino acid at position 182 in the plasmid pHL35 was substituted with the nucleotide gac encoding aspartic acid (Asp), a polymerase chain reaction was performed on the plasmid pHL35 using the primer as set forth in SEQ ID NO: 8 and the primer as set forth in SEQ ID NO: 9 to substitute the nucleotide aac encoding asparagine (Asn) at position 268 in the plasmid pHL35 with the nucleotide gac encoding aspartic acid (Asp) to obtain a plasmid pHL43 expressing the amino acid sequence as set forth in SEQ ID NO: 3.

Experiment 5: Performing Multiple Point Mutations on Fructosyl Amino Acid Oxidase The above-mentioned multiple point mutation refers to substituting three of the amino acid residues of FAOD, such as substituting glycine (Gly) at position 182, asparagine (Asn) at position 268, and histidine (His) at position 384 of the amino acid sequence as set forth in SEQ ID NO: 1 to obtain a triple-mutant fructosyl amino acid oxidase. Specifically, for instance, glycine (Gly) at position 182 was substituted with aspartic acid (Asp), asparagine (Asn) at position 268 was substituted with aspartic acid (Asp), and histidine (His) at position 384 was substituted with tyrosine (Tyr) at the same time. The method of substituting the amino acid residues is the same as above and is not repeated herein.

In particular, firstly, the nucleotide encoding histidine (His) at position 384 of the amino acid sequence as set forth in SEQ ID NO: 1 was found to be cat in the polynucleotide shown in SEQ ID NO: 5. At the same time, the primer as set forth in SEQ ID NO: 10 and the primer as set forth in SEQ ID NO: 11 were synthesized, in which both primers have the nucleotide tat. Next, since the nucleotide encoding the amino acid at position 182 and the amino acid at position 268 in the plasmid pHL43 were both substituted with the nucleotide gac encoding aspartic acid (Asp), a polymerase chain reaction was performed on the plasmid pHL43 using the primer as set forth in SEQ ID NO: 10 and the primer as set forth in SEQ ID NO: 11 to substitute the nucleotide cat encoding histidine (His) at position 384 in the plasmid pHL43 with the nucleotide tat encoding aspartic acid (Asp) to obtain a plasmid pHL37 expressing the amino acid sequence as set forth in SEQ ID NO: 4.

In short, the plasmid pHL35 may express the amino acid sequence as set forth in SEQ ID NO: 2, and the amino acid at position 182 was substituted with aspartic acid (Asp). The plasmid pHL43 may express the amino acid sequence as set forth in SEQ ID NO: 3, and the amino acids at position 182 and position 268 were both substituted with aspartic acid (Asp). The plasmid pHL37 may express the amino acid sequence as set forth in SEQ ID NO: 4, in which the amino acids at position 182 and position 268 were both substituted with aspartic acid (Asp), and the amino acid at position 384 was substituted with tyrosine (Tyr).

Experiment 6: Mass Expression and Purification of Fructosyl Amino Acid Oxidase

First, the plasmid pYC1 and the plasmids pHL35, pHL43, and pHL37 after amino acid residue substitution were respectively transformed into a host cell to obtain a transformant having ampicillin resistance. The host cell may be E. coli, such as BL21 Star™ (DE3) (Chemically Competent E. coli) (Invitrogen), but the disclosure is not limited thereto.

Next, a culture medium for growing a transformant was prepared. First, 500 mL of TB (Terrific Broth) culture medium was dispensed into an Erlenmeyer flask with a volume of 2 L, and high-pressure steam sterilization was performed at 121° C. for 20 minutes. After the culture medium was cooled down, ampicillin was added to the culture medium after sterile filtration to achieve a final ampicillin concentration of 100 µg/mL.

Then, 2 mL of a BL21 Star™ (DE3) (pYC1) culture solution grown for 16 hours at 37° C. beforehand was inoculated in the above-mentioned TB culture medium, in which the culture solution was a LB (Lysogeny broth) culture medium containing 100 μg/mL ampicillin, and then growth was performed by shaking at 225 rpm at 37° C. as well as the absorbance (OD600 or A600) at 600 nm was kept tracking at the same time. When the absorbance reached 0.6, the temperature was adjusted to 20° C. and isopropyl-betaβ-D-thiogalactopyranoside (IPTG) was added to achieve a final IPTG concentration of 1 mM.

Thereafter, growing was continued for 20 hours. After culture was completed, bacteria was collected by centrifuge and CelLytic™ B 2X Cell Lysis Reagent (Sigma) was added to disrupt the bacteria, and a suspension containing the disrupted bacteria was centrifuged to separate and obtain the supernatant. Next, the resulting supernatant was purified using cOmplete™ His-Tag Purification Resin (Roche) to obtain a purified target protein, and then sodium dodecyl sulfate polyacrylamide gel electrophoresis (SDS-PAGE) was used to confirm whether the purified target protein was actually a single protein.

The target protein is, for instance, fructosyl peptide oxidase of *Phaeosphaeria nodorum* (PnFPOX), i.e., fructosyl amino acid oxidase, and the resulting target protein is the above-mentioned recombinant protein, i.e., the protein for which at least one of glycine (Gly) at position 182, asparagine (Asn) at position 268, and histidine (His) at position 384 in the amino acid sequence as set forth in SEQ ID NO: 1 is substituted. The substitution method of the amino acid residues is provided above and is not repeated herein.

In the above-mentioned operation, the transformant containing the plasmid pYC1 may express the amino acid sequence as set forth in SEQ ID NO: 1, i.e., wild-type fructosyl amino acid oxidase (PnFPOX for short). The transformant containing the plasmid pHL35 may express the amino acid sequence as set forth in SEQ ID NO: 2, i.e., a recombinant protein for which the amino acid at position 182 of the fructosyl amino acid oxidase was substituted with aspartic acid (Asp) (PnFPOX-SS for short). The transfoiniant containing the plasmid pHL43 may express the amino acid sequence as set forth in SEQ ID NO: 3, i.e., a recombinant protein for which the amino acid at position 182 and the amino acid at position 268 of the fructosyl amino acid oxidase were both substituted with aspartic acid (Asp) (PnFPOX-DS for short). The transformant containing the plasmid pHL37 may express the amino acid sequence as set forth in SEQ ID NO: 4, i.e., a recombinant protein for which the amino acid at position 182 and the amino acid at position 268 of the fructosyl amino acid oxidase were both substituted with aspartic acid (Asp) and the amino acid at position 384 was substituted with tyrosine (Tyr) (PnFPOX-TS for short).

Experiment 7: Evaluation of Activity, Substrate Specificity, and Thermal Stability of Fructosyl Amino Acid Oxidase Oxidase activity, substrate specificity, and thermal stability of the recombinant proteins (PnFPOX-SS, PnFPOX-DS, and PnFPOX-TS) were detected, and the results were compared with wild-type fructosyl amino acid oxidase (PnFPOX) and fructosyl amino acid oxidase (FPOX-CE for short) of other species (made by Kikkoman Corporation).

Evaluation of Oxidase Activity

The oxidase activity for the substrate was calculated by reacting oxidase and the substrate to produce hydrogen peroxide, then the hydrogen peroxide and a coloring agent were catalyzed via hydroperoxidase and a color change was occurred therein. Accordingly, the oxidase activity can be calculated by simply detecting the change in absorbance of the coloring agent at a specific wavelength.

The detection method of oxidase activity is specifically described as follows: first, an activity assay solution was prepared with reference to the literature published by Hirokawa et al. in Biochemical and Biophysical Research Communications in 2003 (vol. 311, pages 104 to 111), i.e., a 10 mM potassium phosphate buffer solution at a pH of 8.0 containing 5 mg/L of peroxidase (TOYOBO), 100 mg/L 4-aminoantipyrine (Sigma), and 0.167 g/L TOOS (Sigma). Next, measurement was performed, in which 145 μl of an activity assay solution was pre-heated at 37° C. for 30 minutes, and then 5 μl of an enzyme solution diluted by an enzyme diluent (10 mM potassium phosphate buffer containing 0.15% BSA (pH of 8.0)) beforehand was added in the activity assay reagent to react. After reacting at 37° C. for 5 minutes, the change in absorbance of OD555 within a unit time was measured (ΔOD experiment/min). At the same time, the enzyme solution was replaced by 5 μl of an enzyme diluent, and then the same operation as above was performed and the change in absorbance (ΔOD blank/min) was measured as a blank.

Oxidase activity was calculated via the resulting change in absorbance based on the formula below with the amount of enzyme oxidizing 1 μmole of substrate within 1 minute defined as 1 unit (U). Value of oxidase activity (U/ml)={(ΔOD experiment/min−ΔOD blank/min)×150 (μl)×dilution ratio}/{4.5×5 (μl)}. In the formula above, "150 μl" represents the total amount of liquid of the detection solution, "4.5" represents absorption coefficient in millimoles, and "5 μl" represents the liquid volume of the oxidase sample.

Next, the oxidase activity of FPOX-CE, PnFPOX, PnFPOX-SS, PnFPOX-DS, and PnFPOX-TS for different substrates was measured. The detected substrates include: fructosyl lysine (F-K), fructosyl valine (F-V), and fructosyl valyl histidine (F-VH). The detection results of oxidase activity of different recombinant proteins are shown in Table 1.

TABLE 1

Oxidase activity comparison of different recombinant proteins (value of oxidase activity (unit: U/mg))

| | FPOX-CE | PnFPOX | PnFPOX-SS | PnFPOX-DS | PnFPOX-TS |
|---|---|---|---|---|---|
| F-K | 0.82 | 0.12 | 0.29 | 0.25 | 0.05 |
| F-V | 12.69 | 15.14 | 16.43 | 16.59 | 16.03 |
| F-VH | 3.18 | 2.73 | 4.22 | 4.02 | 4.05 |

It may be known from the results of Table 1 that, in comparison to the fructosyl amino acid oxidase (FPOX-CE) of other species, the oxidase activity of wild-type fructosyl amino acid oxidase (PnFPOX) for fructosyl lysine (F-K) is lower and the oxidase activity thereof for fructosyl valine (F-V) is higher. Moreover, in comparison to wild-type fructosyl amino acid oxidase (PnFPOX), the oxidase activity of triple-mutant fructosyl amino acid oxidase (PnFPOX-TS) for F-K is lower, but the oxidase activity thereof for fructosyl valine (F-V) and fructosyl valyl histidine (F-VH) is higher.

Evaluation of Substrate Specificity

The substrate specificity of FPOX-CE, PnFPOX, PnFPOX-SS, PnFPOX-DS, and PnFPOX-TS for different substrates is represented by the activity ratio calculated by the following formula based on the above measured result of oxidase activity. In particular, (F-K/F-V)=(value of oxidase activity with F-K as the substrate)/(value of oxidase activity with F-V as the substrate), and a lower activity ratio calculated from the formula indicates that the protein exhibits higher substrate specificity for F-V. In addition, (F-K/F-VH)=(value of oxidase activity with F-K as the substrate)/(value of oxidase activity with F-VH as the substrate), and a lower activity ratio calculated from the formula indicates the protein exhibits higher substrate specificity for F-VH. The analysis results of substrate specificity of different recombinant proteins are shown in Table 2.

TABLE 2

Substrate specificity comparison of different recombinant proteins

|  | FPOX-CE | PnFPOX | PnFPOX-SS | PnFPOX-DS | PnFPOX-TS |
|---|---|---|---|---|---|
| F-K/F-V | 6.4% | 0.8% | 1.8% | 1.5% | 0.3% |
| F-K/F-VH | 25.6% | 4.3% | 6.9% | 6.3% | 1.1% |

It may be known from the results of Table 2 that, in comparison to the fructosyl amino acid oxidase (FPOX-CE) of other species, both the activity ratios of F-K/F-V and F-K/F-VH of wild-type fructosyl amino acid oxidase (PnFPOX) are lower, indicating the substrate specificity of PnFPOX for F-V and F-VH is higher. However, both the activity ratios of F-K/F-V and F-K/F-VH of triple-mutant fructosyl amino acid oxidase (PnFPOX-TS) are significantly lower than fructosyl amino acid oxidase (FPOX-CE) of other species, indicating the substrate specificity of PnFPOX-TS for F-V and F-VH is significantly higher than FPOX-CE, with a difference of about 20 times or more.

In other words, for substrate specificity, although the fructosyl amino acid oxidase (FPOX-CE) of other species exhibits the more extensive substrate activity, the substrate specificity thereof is poor. On the contrary, wild-type fructosyl amino acid oxidase (PnFPOX), single-mutant fructosyl amino acid oxidase (PnFPOX-SS), double-mutant fructosyl amino acid oxidase (PnFPOX-DS), and triple-mutant fructosyl amino acid oxidase (PnFPOX-TS) exhibit improved substrate specificity, and in particular, PnFPOX-TS exhibits the best improved effect on substrate specificity.

Evaluation of Thermal Stability

The fructosyl amino acid oxidase (FPDX-CE) of other species, wild-type fructosyl amino acid oxidase (PnFPDX), and the recombinant proteins (PnFPDX-SS, PnFPDX-DS, and PnFPDX-TS) were respectively dissolved in a 100 mM potassium phosphate buffer (pH value of 8.0) to achieve a concentration of 0.05 mg/ml, and after a heat treatment at 25° C. to 60° C. for 10 minutes, the oxidase activities of the above-mentioned fructosyl amino acid oxidases and recombinant proteins were measured. At the same time, thermal stability (%) was calculated based on the following formula:

thermal stability=(value of oxidase activity after heat treatment)/(value of oxidase activity without heat treatment)×100%.

TABLE 3

Thermal stability comparison of different recombinant proteins

|  | FPOX-CE | PnFPOX | PnFPOX-SS | PnFPOX-DS | PnFPOX-TS |
|---|---|---|---|---|---|
| 25° C. | 100% | 100% | 100% | 100% | 100% |
| 30° C. | 99% | 99% | 100% | 101% | 102% |
| 37° C. | 97% | 99% | 100% | 100% | 103% |
| 40° C. | 97% | 99% | 99% | 100% | 102% |
| 45° C. | 87% | 100% | 99% | 102% | 104% |
| 50° C. | 30% | 86% | 96% | 101% | 102% |
| 55° C. | 5% | 6% | 11% | 67% | 33% |
| 60° C. | 0% | 0% | 0% | 0% | 0% |

It may be known from the results of Table 3 that, in comparison to the fructosyl amino acid oxidase of other species (FPOX-CE) and wild-type fructosyl amino acid oxidase (PnFPOX), the fructosyl amino acid oxidases produced by site-directed mutagenesis or multiple point mutations, whether single-mutant, double-mutant, or triple-mutant fructosyl amino acid oxidase (corresponding to mutants PnFPOX-SS, PnFPOX-DS, and PnFPOX-TS, respectively), all three mutants retain 95% oxidase activity after a heat treatment at 50° C. When the temperature of the heat treatment reaches 55° C., the oxidase activity of both FPOX-CE and PnFPOX is reduced to less than 10%, while the oxidase activity of PnFPOX-DS and PnFPOX-TS is still retained the level of 67% and 33%, respectively. That is, in comparison to the fructosyl amino acid oxidase of other species and wild-type fructosyl amino acid oxidase (FPOX-CE and PnFPOX, respectively), the fructosyl amino acid oxidases after site-directed mutagenesis or multiple point mutations (PnFPOX-SS, PnFPOX-DS, and PnFPOX-TS) may exhibit higher thermal stability.

Based on the above, the disclosure provides a recombinant protein and a preparation method thereof, in which the recombinant protein is obtained by substituting at least one amino acid of the amino acids at positions 182, 268, and 384 of the amino acid sequence as set forth in SEQ ID NO: 1. Moreover, in comparison to the wild-type fructosyl amino acid oxidase, this recombinant protein exhibits higher thermal stability and substrate specificity. Otherwise, in comparison to the commercial detection kit for detecting glycated hemoglobin, due to that the detection kit provided by the disclosure includes the above-mentioned recombinant protein, the advantages of accurately quantifying glycated hemoglobin and long-term stable preservation are provided accordingly.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A recombinant protein, comprising:
a peptide, wherein the peptide comprises an amino acid sequence after substitution of a sequence as set forth in SEQ ID NO: 1, and the amino acid sequence of the peptide comprises one selected from a group consisting of a sequence as set forth in SEQ ID NO: 2, a sequence as set forth in SEQ ID NO: 3, and a sequence as set forth in SEQ ID NO: 4.

2. The recombinant protein as claimed in claim 1, wherein the amino acid sequence of SEQ ID NO: 1 and a polynucleotide encoding the sequence of SEQ ID NO: 1 are isolated from *Phaeosphaeria nodorum*.

3. A preparation method of a recombinant protein, comprising the following steps:

substituting nucleotides of a nucleotide sequence encoding an amino acid sequence as set forth in SEQ ID NO: 1 in a plasmid;

transforming the substituted plasmid into a host cell to obtain a transformant; and expressing the recombinant protein by the transformant, wherein the substitution comprises one selected from a group consisting of the following substitutions:

nucleotides encoding glycine (Gly) at position 182 are substituted to obtain the recombinant protein containing the amino acid sequence as set forth in SEQ ID NO: 2;

the nucleotides encoding glycine (Gly) at position 182 and nucleotides encoding asparagine (Asn) at position 268 are substituted simultaneously to obtain the recombinant protein containing the amino acid sequence as set forth in SEQ ID NO: 3; and the nucleotides encoding glycine (Gly) at position 182, the nucleotides encoding asparagine (Asn) at position 268, and nucleotides encoding histidine (His) at position 384 are substituted simultaneously to obtain the recombinant protein containing the amino acid sequence as set forth in SEQ ID NO: 4.

4. The preparation method of the recombinant protein as claimed in claim 3, wherein the step of substituting the nucleotides encoding the amino acid comprises:

substituting the nucleotides encoding glycine (Gly) at position 182 via a primer as set forth in SEQ ID NO: 6 and a primer as set forth in SEQ ID NO: 7;

substituting the nucleotides encoding asparagine (Asn) at position 268 via a primer as set forth in SEQ ID NO: 8 and a primer as set forth in SEQ ID NO: 9; and substituting the nucleotides encoding histidine (His) at position 384 via a primer as set forth in SEQ ID NO: 10 and a primer as set forth in SEQ ID NO: 11.

5. The preparation method of the recombinant protein as claimed in claim 3, wherein the plasmid is prepared by a method of:

optimizing a codon of a fructosyl amino acid oxidase gene to obtain a polynucleotide as set forth in SEQ ID NO: 5; and constructing the polynucleotide as set forth in SEQ ID NO: 5 in a vector to obtain the plasmid encoding the amino acid sequence as set forth in SEQ ID NO: 1.

6. The preparation method of the recombinant protein as claimed in claim 5, wherein the fructosyl amino acid oxidase gene is isolated from *Phaeosphaeria nodorum*.

7. A polynucleotide encoding the recombinant protein as claimed in claim 1.

8. A recombinant vector, comprising the polynucleotide as claimed in claim 7.

9. A transformant, obtained by transforming the recombinant vector as claimed in claim 8 into a host cell.

10. A detection kit for detecting a glycated hemoglobin, comprising the recombinant protein as claimed in claim 1.

* * * * *